United States Patent [19]

Noce

[11] Patent Number: 4,940,459
[45] Date of Patent: Jul. 10, 1990

[54] INFLATION DEVICE FOR BALLOON CATHETER

[75] Inventor: Louis O. Noce, Longwood, Fla.

[73] Assignee: Mallinckrodt, Inc., St. Louis, Mo.

[21] Appl. No.: 256,866

[22] Filed: Oct. 12, 1988

[51] Int. Cl.$^5$ ............................................. A61M 29/00
[52] U.S. Cl. ...................................... 604/98; 604/99
[58] Field of Search ........................... 604/61, 97–100, 604/207–211, 224, 227; 222/386, 390, 391; 401/172, 176; 433/89, 90; 606/191, 194

[56] References Cited

U.S. PATENT DOCUMENTS

| 2,475,939 | 7/1949 | Applezweig | 604/211 |
|---|---|---|---|
| 2,745,575 | 5/1956 | Spencer | 222/390 |
| 3,020,663 | 2/1962 | Newson . | |
| 3,905,365 | 9/1975 | Colombo | 604/209 |
| 4,275,729 | 6/1981 | Silver et al. . | |
| 4,312,343 | 1/1982 | LeVeen et al. . | |
| 4,322,022 | 3/1982 | Bergman | 222/390 |
| 4,332,254 | 6/1982 | Lundquist . | |
| 4,370,982 | 2/1983 | Reilly | 604/98 |
| 4,429,724 | 2/1984 | Dorros et al. . | |
| 4,583,974 | 4/1986 | Kokernak . | |
| 4,654,027 | 3/1987 | Dragan et al. | 604/247 |
| 4,655,749 | 4/1987 | Fischione . | |
| 4,723,938 | 2/1988 | Goodin et al. . | |
| 4,743,230 | 5/1988 | Nordquest | 604/99 |
| 4,832,692 | 5/1989 | Box et al. | 604/99 |
| 4,838,864 | 6/1989 | Peterson | 604/100 |

FOREIGN PATENT DOCUMENTS 0228162 8/1987 European Pat. Off. .

OTHER PUBLICATIONS

USCI, The Wizard TM Disposable Inflation Device, Feb. 1987.
ACS, Indeflator ® Plug and Angiojet, 1982.
American Edwards Laboratories, Inflation Pro TM, Oct. 1986.

Primary Examiner—Stephen C. Pellegrino
Assistant Examiner—Ralph Lewis
Attorney, Agent, or Firm—Bernard, Rothwell & Brown

[57] ABSTRACT

An inflation device for a balloon catheter has a pistol grip type handle with a trigger for releasing a screw plunger to enable rapid inflation and deflation of the balloon catheter. The trigger bias and thread angle of mating threads are selected to automatically release the plunger when a safe balloon catheter pressure is exceeded. A trigger guard is slidable over the trigger to prevent accidental operation and pressure release.

19 Claims, 1 Drawing Sheet

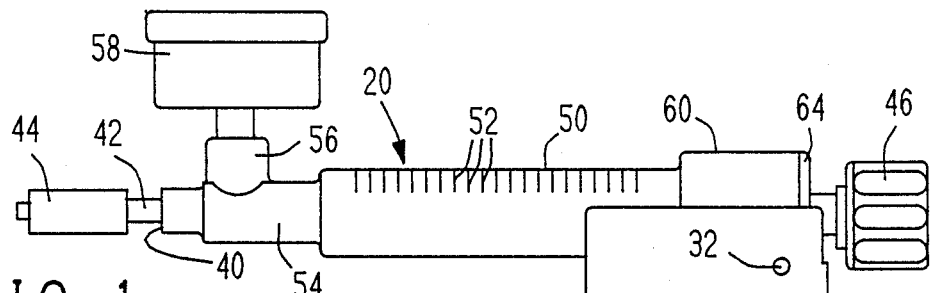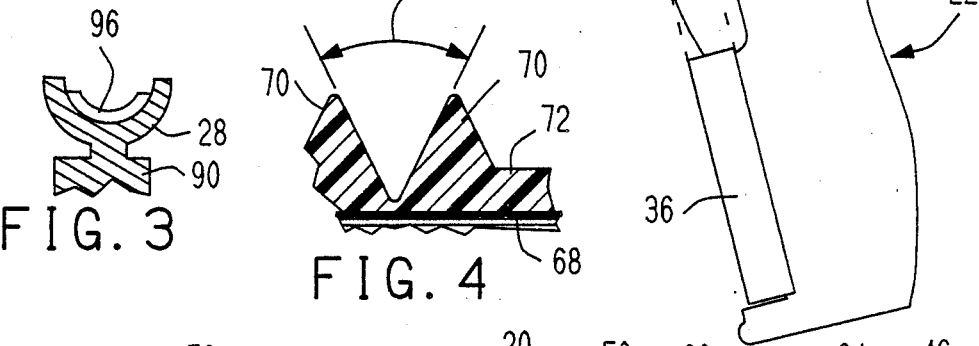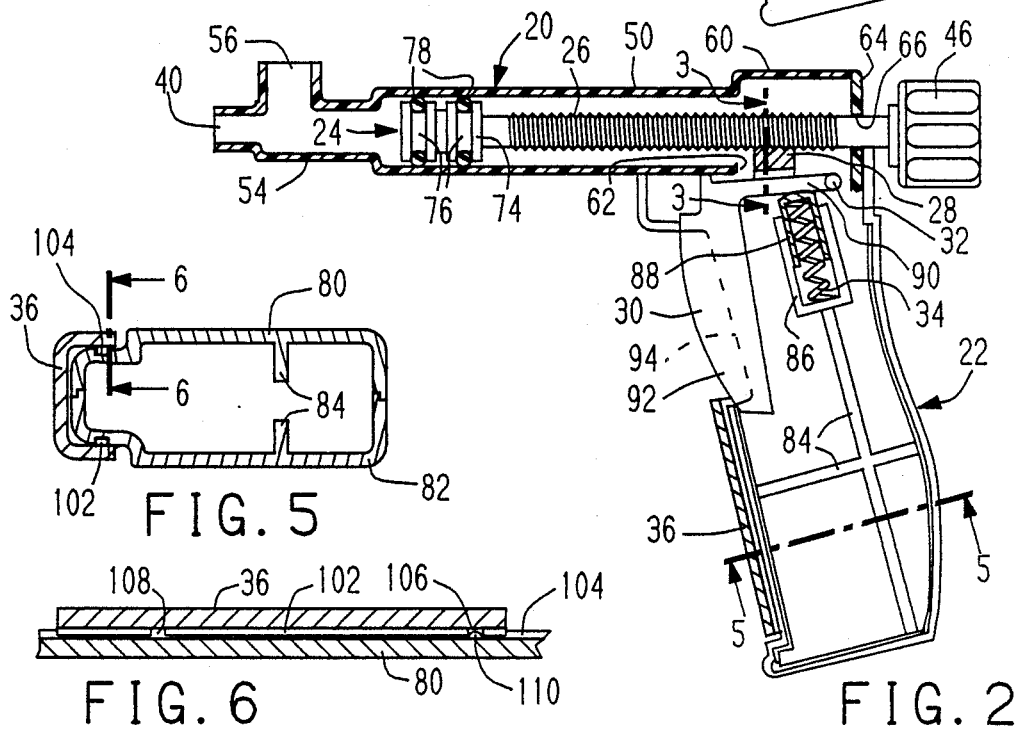

INFLATION DEVICE FOR BALLOON CATHETER

BACKGROUND OF THE INVENTION

1. Technical Field

The invention relates to inflation devices for use with inflatable balloon catheters, such as are used for interventional medical procedures like percutaneous transluminal angioplasty (PTA) and percutaneous transluminal valvuloplasty (PTV).

2. Description of the Prior Art

Prior to the development of angioplasty or PTA, patients with occluded coronary arteries were primarily treated by arterial or saphenous vein graft bypass operations. The bypass operations involve the suturing of the opposite ends of a segment of a blood vessel, for example either a vein segment removed from a leg of the patient or an artery segment, to opposite sides of the blocked section of the coronary artery. Such operations are costly, require a long patient convalescence period, and involve considerable risk which for many older patients or patients in poor health is likely to result in death.

Angioplasty is now used in place of the bypass operation in many patients, and is used on many patients for whom bypass operations are too risky. During angioplasty, a catheter with a deflated balloon is inserted through arteries to place the deflated balloon in the occluded area. The balloon is then inflated with a solution of sterile contrast media and some other sterile fluid and maintained at several atmospheres of pressure for a brief period to enlarge the artery so as to allow blood flow to return to an acceptable level after the balloon is deflated. Balloon repositioning, inflation, and deflation may be repeated several times to achieve the desired results. The PTA procedure has many advantages over bypass operations in that the procedure does not require invasive surgery, is much less traumatic on the patient, and the recovery period is far shorter.

Similarly, valvuloplasty or PVA has recently been developed as an alternative to valve replacement or valvotomy, both major surgical operations. Valve replacement involves removal of the damaged heart valve and replacement with a porcine valve or an artificial valve. Valvotomy includes surgical cutting of the heart valve to remove or open damaged or stenotic areas.

In valvuloplasty, the balloon on a balloon catheter is expanded in the defective valve in order to enlarge the valve opening. This restores sufficient valve function to return the flow through the valve to an acceptable level. As is angioplasty, the procedure is non-invasive and the patient's recovery period is short when compared to surgical methods.

It is preferable for the inflation device used with a balloon catheter in angioplasty or valvuloplasty to precisely inflate the balloon to a desired pressure, maintain that pressure, and then deflate the balloon to the point of achieving a vacuum, for catheter removal or repositioning. Balloon catheters from different manufacturers and for different procedures require varying pressures. In an emergency situation the inflation device can be rapidly inflated or deflated.

There are several inflation devices commercially available in the prior art. Generally, these inflation devices include a pressure gauge to determine the precise fluid pressure transmitted to the balloon, and employ screw plungers to enable the physician to precisely set the pressure. Quick release levers provide for disengagement of driving thread sector members from the plunger threads to allow rapid plunger movement during inflation or deflation.

Generally, the prior art inflation devices have one or more deficiencies, such as having handles which have a shape and location which make it difficult to simultaneously hold and operate the inflation device, having little or no safety features, having hidden fluid pressure chamber regions or passageways allowing undetected air bubbles to be trapped where they interfere with pressurization or pose a threat in the event of balloon failure, and/or other deficiencies.

SUMMARY OF THE INVENTION

In one aspect, the invention is summarized in an inflation device for a balloon catheter wherein the device includes a pistol grip handle with a trigger operating a quick release for a threaded member biased into engagement with a screw plunger which is slidable in a barrel for providing pressurized fluid to the catheter. The inflation device can be held by one hand gripping the handle, and a finger on that hand can operate the quick trigger release. The other hand of the operator can slide or rotate the plunger for quick or precise pressure change.

In another aspect, the invention is summarized in an inflation device for a balloon catheter wherein the device includes a pivoted thread sector member biased against a screw plunger in a barrel for holding the plunger and enabling the plunger to be screwed in the barrel to precisely set fluid pressure in the catheter. The biasing force is selected in conjunction with the engaging thread parameters, which include a screw thread angle between 20° and 160°, to provide automatic release of the plunger when the pressure in the barrel exceeds a predetermined safe pressure for the catheter.

In still another aspect, the invention is summarized in an inflation device for a balloon catheter wherein the device includes a guard mounted for movement over a quick release trigger to prevent its operation which would release a plunger in a barrel to allow rapid increase or decrease of the pressure in the balloon of the catheter. Accidental operation of the trigger is prevented by the guard so that a desired pressure is maintained in the balloon; for example, a negative pressure with respect to atmospheric pressure can be maintained in the balloon during advancement of the catheter through arteries.

An object of the invention is to construct an inflation device for a balloon catheter which provides for easier and more rapid operation.

Another object of the invention is to provide an inflation device for a balloon catheter which includes automatic safety features.

Still another object of the invention is to provide an inflation device which can be manipulated without risk of releasing a pressure being maintained by the device.

One advantage of the invention is that angioplasty and valvuloplasty procedures are improved due to the physician's ability to more rapidly and precisely bring about balloon treatment pressures.

Another advantage of the invention is that patient safety is improved by automatic pressure release for accidental pressure increase which could otherwise cause blood vessel damage or balloon failure.

Still another advantage of the invention is that operation of a quick release trigger in an inflation device is prevented by a trigger guard during manipulation of a catheter and/or the device.

Additional features which can be included in the invention are the provision of an insert molded plunger resulting in plunger strength along with corrosion resistance pressure fluid compatibility; the provision of a clear molded pressure barrel mounted in a manner resulting in visibility of the pressurizing fluid to enable purging and removal of all air bubbles; the provision of clear high pressure tubing which enables visualization and purging of air bubbles; and the provision of a pressure gauge directly measuring fluid pressure through a range including vacuum to pressures above the upper pressure limits of the catheter.

Other objects, advantages, and features of the invention will be apparent from the following description of the preferred embodiment taken in conjunction with the accompanying drawings wherein:

BRIEF DESCRIPTION OF THE DRAWINGS

FIG. 1 is a side elevational view of a device for inflating a balloon catheter in accordance with one embodiment of the invention.

FIG. 2 is a side sectional view, with portions removed, of the device of FIG. 1.

FIG. 3 is a sectional view taken at line 3—3 in FIG. 2 of a thread section broken away from a trigger in the inflation device.

FIG. 4 is a section view taken at an axial plane of a broken away portion of a threaded shank of a plunger in the device of FIG. 2.

FIG. 5 is a cross sectional view taken at line 5—5 in FIG. 2 of a handle of the inflation device.

FIG. 6 is a sectional view taken at line 6—6 in FIG. 5 of broken away portions of a handle half and trigger guard of the inflation device.

DESCRIPTION OF THE PREFERRED EMBODIMENT

As shown in FIGS. 1 and 2, one embodiment of the invention is an inflation device which includes a barrel indicated generally at 20 mounted on a pistol grip handle indicated generally at 22 and with a plunger indicated generally at 24 slidably retained in the barrel. The plunger 24 includes a threaded shank 26 which is normally engaged by a thread section 28 of a trigger 30 with pivot pins 32 pivotally mounting the trigger in the handle. A compression spring 34 biases the trigger 30 to urge the thread section 28 into engagement with the threaded shank 26. A trigger guard 36 is slidably mounted on the handle 22 for sliding over the trigger 30 to prevent operation of the trigger.

In use, the barrel is filled with fluid and the open end 40 of the barrel 20 is connected by tubing 42 and connector 44 to a balloon catheter (not shown). The physician grasps the handle 22 in one hand with the trigger 30 underneath one finger. With the other hand, the physician grasps the knob 46 of the plunger 24 to operate the catheter inflation device. With the trigger 30 depressed by one finger on the hand holding the handle, the plunger 24 is easily retracted or advanced by pulling or pushing on the knob 46 to quickly deflate or inflate the balloon of the catheter. With the trigger 30 released, the knob 46 is easily turned to screw the threaded shank 26 forward on the thread section 28 to precisely increase the fluid pressure to that required for the therapeutic action being performed by the catheter.

If the fluid pressure is increased above a predetermined safe pressure, camming forces generated by the threads of the threaded shank 26 against the thread section 28 overcome the bias of the spring 34 to automatically pivot the trigger 30 and release the plunger 24 which then moves rearward until the pressure is reduced to a level at which the camming forces of the threads of the threaded shank 26 on the thread section 28 no longer exceed the bias of the spring 34.

The barrel 20 is formed by molding from a clear resin, such as clear polycarbonate, and has a main barrel section 50 in which the plunger 24 operates. A scale 52 is formed on the outside surface of the section 50 so that the amount of fluid passing into and out of the barrel can be determined. A reduced diameter barrel section 54 is formed at the forward end of the main barrel section 50. The nipple 40, in which the tube 42 is secured, is formed in the forward end of the reduced section 54. A port 56 is formed in the side of the section 54 and has a pressure gauge 58 secured thereto. The rear portion 60 of the barrel is enlarged and has an opening 62 at the bottom for permitting the thread section 28 of the trigger 30 to extend upward into the rear portion of the barrel. A cap 64 is secured over the rear end of the tubular barrel 20 and has a center opening 66 through which the threaded shaft 26 freely extends. The cap 64 forms a guide for the threaded shaft 26 to limit the shaft to movement in axial and rotative directions as well as to retain the plunger 24 in the barrel.

The plunger 24, as shown in FIG. 4, is insert molded, i.e. is formed by molding a polymer such as nylon 6—6, acetyl polymers or high density olefins on a center shaft 68 formed from steel or other metal. The molded polymer forms the outer configuration, including the threads 70 and outer layer 72, of the plunger to completely encapsulated the metal shaft 68 to prevent rust or corrosion. Forward enlarged piston portion 74 has grooves 76 in which are positioned O-rings 78 forming a double seal with the interior surface of the main barrel section 50 to prevent leakage of fluid to the rear of the piston. The knob 46 is suitable secured on the rear end of the shaft 26 after assembly in the cap 64.

The pistol grip handle 22, as shown in FIG. 5, is formed from two molded halves 80 and 82 which are suitably secured together. The halves are molded from any suitable polymer such as ABS and have reinforcing ribs 84. A spring guide 86 is formed in one of the halves to provide a recess for receiving the spring 34. The guide 86 also slidingly retains member 88 which covers the top end of the spring 34. The trigger 30, molded from a suitable polymer such as polycarbonate, has a generally inverted L configuration with an arm 90 extending parallel to the barrel and plunger from the pivot 32 at the rear end. The spring cover member 88 engages the lower side of the arm 90 while the thread section 28 extends upward from the upper surface of the arm 90. A leg 92 extends downward from the forward end of the arm 90 and has its forward portion exposed through opening 94 in the forward side of the handle 22 for being depressed to pivot the trigger against the bias of the spring 34.

The rear portion of the barrel 20 is secured on the upper end of the handle 22. As shown in FIG. 1, the handle covers only a lower portion of the rear portion of the barrel 20 so that substantially all of the main section 50 is exposed to enable the physician to view all the fluid contents of the barrel. This together with the tubing 42 being clear enables visualization and purging of all air bubbles in the inflation device.

As illustrated in FIG. 3, the thread section 28 is a half annulus with thread segments 96 formed over a predetermined angular portion of the inside surface thereof. These thread segments 96 as well as the threads 70 on the shaft 26 have a selected thread angle, i.e. the angle 98, FIG. 4, that the faces of adjoining threads form with each other in an axial plane. The angle 98 is generally in the range from 20° to 160° and is preferably in the range from about 40° to 100°. Especially preferred is the standard thread angle of 60°. This thread angle, along with the spring force of the spring 34, frictional forces, and the positions of the thread section 28 and engagement of the spring 34 against the arm 90, determine the automatic release pressure of the inflation device. These design factors are generally empirically adjusted until the inflation device achieves automatic release at the predetermined maximum safe balloon catheter pressure. Generally this maximum safe pressure is in the range from 4 to 25 bar, and preferably in the range from 8 to 22, such as 18 bar for one example of a suitable inflation device.

The trigger guard 36, as shown in FIGS. 5 and 6, has a C-shaped cross-sectional configuration. Ribs 102 are formed longitudinally along the inner surfaces of the legs of the guard 36 and slidingly extend in mating grooves 104 formed in the outer surfaces of the handle halves 80 and 82. The ribs 102 have an upper recess 106 and a lower recess 108 for engaging a projection 110 in each of the grooves 110 so as to lockingly retain the guard 36 in lower and upper positions. The upper position is shown in dashed lines in FIG. 1. The guard is placed in this position, for example when a balloon catheter (not shown) is being advanced through arteries. The balloon is maintained deflated by a vacuum or negative pressure, i.e. a pressure below atmospheric pressure, in the inflation device, and release of the negative pressure, such as by accidental operation of the trigger 30 during the advancement, could result in expansion of the balloon which would interfere with continued advancement.

The pressure gauge has a range from about −1 to 20 bar. In one embodiment, the gauge has dual scales providing readings in both atmospheres and pounds per square inch above atmospheric pressure.

Since many modifications, variations, and changes in detail may be made to the above described embodiment, it is intended that all matter in the foregoing description and shown in the accompanying drawings be interpreted as only illustrative and not as limiting on the scope of the following claims.

What is claimed is:

1. A device for inflating a balloon catheter, comprising:
    a tubular barrel for receiving an inflation fluid and having fluid outlet means at one end for connecting the barrel to the catheter,
    a plunger having a sliding piston in the barrel and a threaded shank extending from the piston out the other end of the barrel,
    a pistol grip handle mounted on the barrel, said pistol grip handle extending from one side of the barrel for being gripped, on one side by a thumb and on the opposite side by the four fingers of a hand of an operator,
    a trigger pivotally mounted in the handle and having a thread section for being pivoted into engagement with the threaded shank of the plunger,
    means for biasing the trigger to urge the thread section thereof into engagement with the threaded shank,
    a knob on the plunger shank for enabling an operator to screw the plunger into and out of the barrel to increase and decrease the pressure of the inflation fluid, and
    said trigger being positioned in the handle so as to be operable by a finger of the hand gripping the handle to release engagement of the thread section from the threaded shank to enable free sliding movement of the plunger in the barrel.

2. A device for inflating a balloon catheter as claimed in claim 1 including a trigger guard movably mounted on the handle for being moved into a position covering the trigger to prevent operation of the trigger.

3. A device for inflating a balloon catheter as claimed in claim 2 wherein the trigger guard has a C-shaped cross section and is slidable over the trigger.

4. A device for inflating a balloon catheter as claimed in claim 3 wherein the trigger guard has ribs on the interior sides of the legs defined by the C-shaped cross section of the guard, and the handle has grooves formed on exterior surfaces thereof and slidingly receiving the ribs.

5. A device for inflating a balloon catheter as claimed in claim 4 wherein the ribs have recesses, and the grooves have projections for engaging the recesses so as to retain the trigger guard in covering and retracted positions.

6. A device for inflating a balloon catheter as claimed in claim 1 wherein said threaded shank and said thread section having mating threads with an angle of thread selected in conjunction with said biasing means to provide for automatic release of the thread section from the threaded shank when the pressure in the barrel exceeds a maximum safe pressure for the catheter.

7. A device for inflating a balloon catheter as claimed in claim 6 wherein said maximum safe pressure is in the range from 4 to 25 bar.

8. A device for inflating a balloon catheter as claimed in claim 7 wherein said maximum safe pressure is in the range from 8 to 22 bar.

9. A device for inflating a balloon catheter as claimed in claim 8 wherein said maximum safe pressure is about 18 bar.

10. A device for inflating a balloon catheter, comprising:
    a tubular barrel for receiving an inflation fluid and having fluid outlet means at one end for connecting the barrel to the catheter,
    a plunger having a sliding piston in the barrel and a threaded shank extending from the piston out the other end of the barrel,
    a handle mounted on the barrel for being gripped by a hand of an operator,
    a pressure release member pivotally mounted in the handle and having a thread section for being pivoted into engagement with the threaded shank of the plunger,
    means for biasing the pressure release member to urge the thread section thereof into engagement with the threaded shank,
    a knob on the plunger shank for enabling an operator to screw the plunger into and out of the barrel to increase and decrease the pressure of the inflation fluid, and said threaded shank and said thread section having mating threads with an angle of thread selected in conjunction with said biasing means to provide for automatic release of the pressure release member when the pressure in the barrel exceeds a maximum safe pressure for the catheter.

11. A device for inflating a balloon catheter as claimed in claim 10 wherein said maximum safe pressure is in the range from 4 to 25 bar.

12. A device for inflating a balloon catheter as claimed in claim 11 wherein said maximum safe pressure is in the range from 8 to 22 bar.

13. A device for inflating a balloon catheter as claimed in claim 12 wherein said maximum safe pressure is about 18 bar.

14. A device for inflating a balloon catheter as claimed in claim 10 including a guard member movably mounted on the handle for being moved into a position covering the pressure release member to prevent operation of the pressure release member.

15. A device for inflating a balloon catheter as claimed in claim 14 wherein the guard member has a C-shaped cross section and is slidable over the pressure release member.

16. A device for inflating a balloon catheter, comprising:

a tubular barrel for receiving an inflation fluid and having fluid outlet means at one end for connecting the barrel to the catheter, a plunger having a sliding piston in the barrel and a threaded shank extending from the piston out the other end of the barrel, a handle mounted on the barrel for being gripped by a hand of an operator, a pressure release member mounted on the handle and having a thread section for being pivoted into engagement with the threaded shank of the plunger, means for biasing the pressure release member to urge the thread section thereof into engagement with the threaded shank, a knob on the plunger shank for enabling an operator to screw the plunger into and out of the barrel to increase and decrease the pressure of the inflation fluid, and a guard movably mounted on the handle for being moved into a position covering the pressure release member to prevent operation of the pressure release member.

17. A device for inflating a balloon catheter as claimed in claim 16 wherein the guard has a C-shaped cross section and is slidable over the pressure release member.

18. A device for inflating a balloon catheter as claimed in claim 17 wherein the guard has ribs on the interior sides of the legs defined by the C-shaped cross section of the guard, and the handle has grooves formed on exterior surfaces thereof and slidingly receiving the ribs.

19. A device for inflating a balloon catheter as claimed in claim 18 wherein the ribs have recesses, and the grooves have projections for engaging the recesses so as to retain the guard in covering and retracted positions.

* * * * *